US005629439A

United States Patent [19]
Bank et al.

[11] Patent Number: 5,629,439
[45] Date of Patent: May 13, 1997

[54] METHOD FOR PREPARATION OF ALLYLSILANES

[75] Inventors: Howard M. Bank, Freeland; Sean P. Davern, Auburn; Binh T. Nguyen, Midland, all of Mich.

[73] Assignee: Dow Corning Corporation, Midland, Mich.

[21] Appl. No.: 624,860

[22] Filed: Mar. 28, 1996

[51] Int. Cl.⁶ .................................................. C07F 7/08
[52] U.S. Cl. .................................................. 556/480
[58] Field of Search .................................................. 556/480

[56] References Cited

U.S. PATENT DOCUMENTS

| | | | |
|---|---|---|---|
| 5,068,386 | 11/1991 | Shirahata | 556/480 |
| 5,294,727 | 3/1994 | Kubota et al. | 556/480 |
| 5,358,670 | 10/1994 | Turnbull et al. | 260/665 |

OTHER PUBLICATIONS

Organometallic Compounds, Coates et al., vol. 1 76–103, (1967), Methuen & Co. LTD, London, UK.
Encyclopedia of Chem Technology, Kirk & Othmer, vol. 10, 721–734 (1966), The Interscience Encyclopedia, Inc. NY, NY.
Grignard Reactions of Nonmetallic Substances, Kharash et al, Printice–Hall, Inc. NY, 1954, 1306–1331.
Organic Synthesis, Turk et al., vol. 27, 7–8, 1947.

*Primary Examiner*—Paul F. Shaver
*Attorney, Agent, or Firm*—William F. Boley

[57] ABSTRACT

A method for the preparation of allylsilanes. The method comprises contacting magnesium metal with a mixture comprising diethylene glycol dibutyl ether, allyl halide, and a halosilane at a temperature within a range of about 5° C. to 20° C. The method provides a high yield of allylsilane product that is easily recoverable and also provides for high ratios of allylsilane to hexadiene by-product.

14 Claims, No Drawings

METHOD FOR PREPARATION OF ALLYLSILANES

BACKGROUND OF INVENTION

The present invention is a method for the preparation of allylsilanes. The method comprises contacting magnesium metal with a mixture comprising diethylene glycol dibutyl ether, allyl halide, and a halosilane at a temperature within a range of about 5° C. to 200° C. The method provides a high yield of allylsilane product that is easily recoverable and also provides for high ratios of allylsilane to hexadiene by-product.

The reaction of organic halides with magnesium metal in the presence of solvents such as dialkyl ethers to form reactive complexes typically referred to as Grignard reagents is well known. The production and reactions of Grignard reagents has been the subject of books and numerous review articles. Such reviews are provided, for example, in Coates et al., ORGANOMETALLIC COMPOUNDS, Vol. 1, p. 76–103 (1967), Methuen and Co. LTD, London, U.K.; and in Kirk and Othmer, ENCYCLOPEDIA OF CHEMICAL TECHNOLOGY, Vol. 10, 721–734 (1966), The Interscience Encyclopedia, Inc., NY, N.Y. The structure of the Grignard reagent has not been determined with certainty. However, it is generally believed that the Grignard reagent exists as a complex in solution and solvent can play a critical role in such complex formation. The unpredictable effect of solvent on the formation and reactivity of Grignard reagents is discussed in the above cited review articles.

The reaction of Grignard reagents with halosilanes is also well known and many such reactions are described in Kharash et al., Grignard Reactions of Nonmetallic Substances, Prentice-Hall, Inc. NY, 1954, P. 1306–1331.

The preparation of 1,5-hexadiene, by a process using an allyl chloride Grignard reagent as an intermediate is known. For example, Turk et al., Organic Synthesis, Vol. 27, 7–8, 1947, teach a process for preparing 1,5 hexadiene by the reaction of allyl chloride in anhydrous ether with magnesium turnings. Turk et al. teach that this reaction results in the formation of a thick slurry which becomes unstirrable. This unstirrable slurry is then treated with a hydrochloric acid solution until the magnesium chloride by-product is in solution and the slurry becomes sufficiently fluid to be stirred.

The process as taught by Turk et al. is not generally acceptable as a commercial process. The formation of the non-stirrable slurry during conduct of the reaction can cause reduced mass transfer and heat transfer and therefore reduced yield of product. Furthermore, the nature of the slurry makes it necessary to treat the slurry in an additional step with a reagent to solubilize the slurry to allow isolation of the product. Typically, a major portion of the product is trapped within the non-stirrable slurry. In addition, the non-flowable nature of the slurry does not allow for the reaction to be run as a continuous process.

Turnbull et al., U.S. Pat. No. 5,358,670, report the formation of alkyl Grignard reagents in diethylene glycol dibutyl ether (DEGDBE). Turnbull et at. reported that Grignard reagents prepared in the presence of DEGDBE have improved yield and stability.

It is an objective of the present invention to provide a method for preparing allylsilanes using a Grignard-type reagent as an intermediate, where the method avoids many of the above discussed problems with Grignard type processes by creating a reaction mixture that is flowable and easily stirred. Thus, mass transfer and heat transfer can be improved in the reaction mixture providing for improved yield of allylsilane. In addition, the method provides for a two-phase system from which the allylsilane can be easily separated. Furthermore the present method provides for an improved ratio of the desired allylsilane to hexadiene by-product, when compared to known Grignard-type processes for preparing organo substituted silanes.

SUMMARY OF INVENTION

The present invention is a method for the preparation of allylsilanes. The method comprises contacting magnesium metal with a mixture comprising diethylene glycol dibutyl ether, allyl halide, and a halosilane at a temperature within a range of about 5° C. to 200° C. The method provides a high yield of allylsilane product that is easily recoverable and also provides for high ratios of allylsilane to hexadiene by-product.

DESCRIPTION OF INVENTION

The present invention can be practiced as a one-step method for the preparation of allylsilanes. The method comprises contacting magnesium metal with a mixture comprising diethylene glycol dibutyl ether, allyl halide, and a halosilane described by formula $$Me_aH_bSiX_{4-a-b},$$

where Me is methyl, X is a halogen selected from a group consisting of chlorine and bromine, a=0 to 3, b=0 or 1, and a+b=1 to 3, at a temperature within a range of about 5° C. to 200° C.

In the present method, by the term "one-step" it is meant that it is not necessary to isolate an intermediate Grignard type reagent in the method and further react this Grignard type reagent with the halosilane to form the allylsilane. Furthermore, it is not necessary to conduct a separate solubilization step on the resulting product mixture to facilitate recovery of the allylsilane.

The method comprises reacting magnesium metal with allyl halide in the presence of a halosilane and diethylene glycol dibutyl ether (DEGDBE). The method of preparing the magnesium metal and the physical form of the magnesium metal can be any of those known in the art. The magnesium metal can be, for example, in the form of powder, chips, or shavings. A preferred form of magnesium metal is in the form of shavings.

Contact of the magnesium metal with the allyl halide can be effected in standard reactors suitable for running Grignard type reactions. The reactor can be of a batch type, semi-batch type, or continuous-type. A preferred reactor is a continuous-type reactor. The environment in which the present method is run should be inert. Therefore, in a preferred method the reactor is purged and blanketed with an inert gas such as, for example, nitrogen or argon.

The mole ratio of magnesium to allyl halide fed to the reactor is not critical and can be varied within wide limits. In a batch process it is preferred that the mole ratio of magnesium to allyl halide provide allyl halide in sufficient excess to ensure essentially total conversion of the magnesium to allyl magnesium halide complexes. When the present method is conducted as a continuous process, the magnesium metal is typically present in excess in relation to the allyl halide fed to the reactor. In such a case, the rate of feed of allyl halide and halosilane to the reactor can be controlled to assure acceptable levels of conversion of the allyl halide to the allylsilane and minimal presence of unreacted allyl magnesium halide complexes. The halosilane feed may be split, with a portion being added after the magnesium bed to insure complete reaction of the allyl magnesium halide complex. Excess allyl halide and halosilane added to the reactor can be recovered and recycled to the process.

Allyl halides useful in the present method include allyl chloride and allyl bromide. The preferred allyl halide is allyl chloride.

Halosilanes useful in the present method are described by formula $Me_aH_bSiX_{4-a-b}$, where Me is methyl, X is a halogen selected from a group consisting of chlorine and bromine atoms, a=0 to 3, b=0 or 1, and a+b=1 to 3. Preferred is when X is chlorine. The halosilane can be for example, trimethylchlorosilane, dimethytchlorosilane, methyldichlorosilane, dimethyldichlorosilane, methyltrichlorosilane and the bromine analogs of such chlorosilanes.

The mole ratio of allyl halide to halosilane can be varied within a range of about 0.1 to 10. Preferred is when the mole ratio of allyl halide to halosilane is within a range of about 0.8 to three. A preferred method is where the magnesium is added to the process in excess to the allyl halide and the halosilane is added in excess to the resulting allyl magnesium halide intermediate. However, for safety reasons, with some halosilanes it may be desirable to run the method where the allyl magnesium halide intermediate is in excess.

The present method is conducted in the presence of diethylene glycol dibutyl ether (DEGDBE). About one to 15 moles of DEGDBE can be added to the method per mole of allyl halide. Preferred is when about one to 10 moles of DEGDBE is added to the method per mole of allyl halide. Even more preferred is when about one to five moles of DEGDBE is added to the method per mole of allyl halide.

The present method can be run at a temperature within a range of about 5° C. to 200° C. It is preferred that the present method be run at a temperature within a range of about 30° C. to 170° C. The pressure at which the present method is run is not critical and can be ambient to about 200 psig. A preferred pressure is within a range of from about 0 psig to 125 psig.

The product of the present method is an allylsilane, where one or more of the halogen substituents on the silicon atom of ehe halosilane have been replaced by an allyl group. Examples of allylsilanes which can be prepared by the present method include, allyltrimethylsilane, allyldimethylsilane, allylmethylchlorosilane, allyldimethylchlorosilane, allylmethyldichlorosilane, and diallyldimethylsilane.

The mixture resulting from conduct of the present method on standing separates into two-phases, with one phase comprising the allylsilane in DEGDBE and the other phase comprising a magnesium dihalide complex solubilized in DEGBDE. The allylsilane can be separated from the DEGDBE by, for example, distillation. The DEGDBE may be recovered from one or both of these phases and recycled to the method.

The following examples are provided to illustrate the present invention. The examples are not intended to limit the scope of the present claims.

EXAMPLE 1.

(Reference)

The reaction of magnesium metal, allyl chloride, and trimethylchlorosilane in diethyl ether was evaluated. Magnesium turnings (0.067 mol), diethyl ether (0.138 mol), and trimethylchlorosilane (0.015 mol) were loaded into a glass bottle and mixed. Octane (0.0013 mol) was added to the bottle as an internal standard. The bottle was purged with nitrogen, then allyl chloride (0.02 mol) in diethyl ether (0.005 mol) was slowly added to the bottle with mixing. After four hours at room temperature the thick slurry that was formed was analyzed by gas chromatography using a flame ionization detector (GC-FID). The GC-FID analysis indicated a 71 percent yield of allyltrimethyisilane, based upon the amount of trimethylchlorosilane fed to the process, and approximately a 10:1 mole ratio of allyltrimethylsilane to 1,5-hexadiene by-product.

EXAMPLE 2.

The reaction of magnesium metal, allyl chloride, and trimethylchlorosilane in diethylene glycol dibutyl ether (DEGDBE) was evaluated. Magnesium turnings (0.7 mol), DEGDBE (1.53 mol), and octane (0.024 mol) as an internal standard were loaded into a glass flask equipped with a reflux condenser, addition funnel, mechanical stirrer, heating mantle, and nitrogen inlet port. The flask was purged with nitrogen and then heated to 44° C. A mixture comprising DEGDBE (1.53 mol), trimethylchlorosilane (0.68 mol), and allyl chloride (0.51 mol) was placed into the addition funnel and slowly added to the glass flask over a two hour period. Approximately one hour after completion of the addition of the mixture to the flask an exotherm was observed, with the temperature rising to 110° C. An ice bath was used to cool the mixture to 44° C. A two-phase system was observed at this time. The reaction mixture was stirred an additional six hours at 44° C. and then transferred to a separatory funnel to separate into two phases. GC-FID analysis of the top phase indicated the presence of 0.1 area percent (area allyl chloride, 1.5 area % trimethylchlorosilane, 13.2 area % allyltrimethylsilane, 79.2 area % DEGDBE, 2.3 area % octane, and 2 area % hexamethyldisiloxane. A portion of the bottom phase was extracted in toluene. Analysis of the toluene extract by GC-FID indicated the presence of 0.0 area % allyl chloride, 0.2 area % trimethylchlorosilane, 0.5 area % allyltrimethylsilane, 24 area % DEGDBE, and 75.1 area % toluene. A separate portion of the bottom layer was evaporated and found to comprise 28 weight percent $MgCl_2$. The mole ratio of allyltrimethylsilane to hexadiene was determined to by 71:1.

EXAMPLE 3.

The reaction of magnesium metal, allyl chloride, and various chlorosilanes in DEGDBE was evaluated. Magnesium turnings in slight excess relative to replaceable chlorine on the chlorosilane was added to glass tubes. A mixture comprising DEGDBE, chlorosilane, and allyl chloride in a mole ratio of 3/2/1 was prepared and added to the glass tubes. The chlorosilanes tested are described in Table 1. The tubes were then purged with nitrogen, cooled in a IPA/dry ice bath and sealed. The sealed tubes were heated at 100° C. for the times described in Table 1. At the end of the heating period the tubes were cooled and the top phase of the mixture in the tube analyzed by GC-FID. The results are reported in Table 1 ("% Yield") as the mole percent of the chlorosilane feed converted to allylsilane. Also reported in Table 1 is the mole ratio of allylsilane to hexadiene formed in the method ("Silane/Diene").

TABLE 1

Reaction of Various Halosilanes to Form Allylsilanes

| Halosilane | Allylsilane | Time (h) | % Yield | Silane/Diene |
|---|---|---|---|---|
| Me$_3$SiCl | AllylSiMe$_3$ | 16 | 70 | 35 |
| Me$_2$HSiCl | AllylSiMe$_2$H | 3 | 92 | 70 |
| MeHSiCl$_2$ | AllylSiMeHCl | 19 | 50 | 22 |
| Me$_2$SiCl$_2$ | AllylSiMe$_2$Cl | 19 | 60 | 78 |
| MeSiCl$_3$ | AllylSiMeCl$_2$ | 19 | 60 | 50 |

We claim:

1. A method for preparation of allylsilanes, the method comprising contacting magnesium metal with a mixture comprising diethylene glycol dibutyl ether, allyl halide, and a halosilane described by formula $$Me_aH_bSiX_{4-a-b},$$

where Me is methyl, X is a halogen selected from a group consisting of chlorine and bromine, a=0 to 3, b=0 or 1, and a+b=1 to 3, at a temperature within a range of about 5° C. to 200° C.

2. A method according to claim 1, where the method is conducted as a continuous process comprising by passing the mixture through a bed of the magnesium metal.

3. A method according to claim 1, where the allyl halide is selected from a group consisting of allyl chloride and allyl bromide.

4. A method according to claim 1, where the allyl halide is allyl chloride.

5. A method according to claim 1, where X is chlorine.

6. A method according to claim 1, where the halosilane is selected from a group consisting of trimethylchlorosilane, dimethylchlorosilane, methyldichlorosilane, dimethyldichlorosilane, and methyltrichlorosilane.

7. A method according to claim 1, where the halosilane is trimethylchlorosilane.

8. A method according to claim 1, where the mixture comprises about one to 15 moles of diethylene glycol dibutyl ether per mole of allyl halide.

9. A method according to claim 1, where the mixture comprises about one to 10 moles of diethylene glycol dibutyl ether per mole of allyl halide.

10. A method according to claim 1, where the mixture comprises about one to five moles of diethylene glycol dibutyl ether per mole of allyl halide.

11. A method according to claim 1, where the temperature is within a range of about 30° C. to 170° C.

12. A method according to claim 1, where the mole ratio of the allyl halide to the halosilane in the mixture is within a range of about 0.1 to 10.

13. A method according to claim 1, where the mole ratio of the allyl halide to the halosilane in the mixture is within a range of about 0.8 to three.

14. A one step method for preparation of allylsilanes, the method comprising contacting magnesium metal with a mixture comprising allyl chloride, one to five moles of diethylene glycol dibutyl ether per mole of allyl chloride, and a halosilane selected from a group consisting of trimethylchlorosilane, dimethylchlorosilane, methyldichlorosilane, dimethyldichlorosilane, and methyltrichlorosilane, where the mole ratio of allyl chloride to halosilane is within a range of about 0.8 to three, at a temperature within a range of about 30° C. to 170° C.

* * * * *